US012616612B2

(12) United States Patent
Sablone

(10) Patent No.: US 12,616,612 B2
(45) Date of Patent: May 5, 2026

(54) ABSORBENT SANITARY ARTICLE AND A METHOD FOR PRODUCING THE SAME

(71) Applicant: Fameccanica.Data S.p.A., San Giovanni Teatino (IT)

(72) Inventor: Gabriele Sablone, San Giovanni Teatino (IT)

(73) Assignee: Fameccanica.Data S.p.A.

( * ) Notice: Subject to any disclaimer, the term of this patent is extended or adjusted under 35 U.S.C. 154(b) by 699 days.

(21) Appl. No.: 17/953,667

(22) Filed: Sep. 27, 2022

(65) Prior Publication Data

US 2023/0097138 A1 Mar. 30, 2023

(30) Foreign Application Priority Data

Sep. 29, 2021 (EP) .................................... 21199774

(51) Int. Cl.
*A61F 13/15* (2006.01)
*A61F 13/49* (2006.01)
(52) U.S. Cl.
CPC .. *A61F 13/15585* (2013.01); *A61F 13/49009* (2013.01); *A61F 2013/49041* (2013.01)
(58) Field of Classification Search
CPC .............. A61F 13/15585; A61F 13/495; A61F 13/494; A61F 2013/49041
See application file for complete search history.

(56) References Cited

U.S. PATENT DOCUMENTS

| | | | | |
|---|---|---|---|---|
| 5,935,118 A | * | 8/1999 | Gryskiewicz ....... | A61F 13/5323 |
| | | | | 604/385.02 |
| 2018/0071155 A1 | * | 3/2018 | Bishop ................ | A61F 13/4942 |
| 2019/0254886 A1 | * | 8/2019 | Köktürk ............ | A61F 13/49017 |
| 2021/0121334 A1 | * | 4/2021 | Sablone ............ | A61F 13/15723 |

FOREIGN PATENT DOCUMENTS

| | | |
|---|---|---|
| EP | 3811916 A1 | 4/2021 |
| WO | 9720532 A1 | 6/1997 |

OTHER PUBLICATIONS

European Search Report dated Mar. 18, 2022. 5 pages.

* cited by examiner

*Primary Examiner* — Jacqueline F Stephens
(74) *Attorney, Agent, or Firm* — RMCK Law Group PLC

(57) ABSTRACT

An absorbent sanitary article including a chassis and at least one gasketing element including two non-elastic outer layers and a transversally stretchable elastic film, wherein the transversally stretchable elastic film is shorter than the two non-elastic outer layers both in longitudinal and transverse directions, so that the gasketing element has two non-elastic longitudinal portions and two non-elastic transverse portions forming a non-elastic frame surrounding the transversally stretchable elastic film.

13 Claims, 4 Drawing Sheets

1

ABSORBENT SANITARY ARTICLE AND A METHOD FOR PRODUCING THE SAME

CROSS-REFERENCE TO RELATED APPLICATION

This application claims priority to European Patent Application No. 21199774.7 filed Sep. 29, 2021. The disclosure of the above application is incorporated herein by reference in its entirety.

FIELD OF THE INVENTION

The invention relates to absorbent sanitary articles, such as, for example, diapers, training pants, absorbent sanitary products for incontinent adults, etc.

The invention also relates to a method for producing absorbent sanitary articles.

PRIOR ART

An absorbent sanitary article typically has a structure that comprises a central body or chassis having rear and front sections. The chassis normally includes a permeable topsheet intended to come into contact with the user's skin when the article is worn, an impermeable backsheet and an absorbent core sandwiched between the topsheet and the backsheet. The rear and front sections of the chassis are normally closed around the user's waist by means of hook-and-loop fasteners, better known as Velcro© fastening devices.

The rear and front sections may be elasticized. WO 2020/242714 and WO2021/092606 disclose methods for bonding elastic parts under tension to an advancing carrier, which may be used for elasticizing the waist sections of absorbent sanitary articles. The methods disclosed in these documents provide: advancing a carrier substrate, advancing a continuous elastic substrate, cutting an elastic part from the continuous elastic substrate, stretching the elastic part in a cross direction, positioning the elastic part on the carrier substrate, and adhesively bonding a stretched central region of the elastic part with the carrier substrate, and mechanically bonding end regions of the elastic part with the carrier substrate.

The formation of elasticized waist sections involves a high cost both for the machine and for the materials used for manufacturing absorbent sanitary articles. In particular, the elastic films used for manufacturing elastic element have a substantial impact on the cost of the absorbent sanitary articles.

Although it would be desirable to avoid applying elastic elements in the waist regions to reduce the costs of absorbent sanitary articles and of the machines for manufacturing the same, without elastic elements in the waist regions the absorbent sanitary articles might have reduced capacity to contain leakage of body exudates in the crotch region, especially solid and semi-solid body exudates.

OBJECT AND SUMMARY OF THE INVENTION

The object of the invention is to provide an absorbent sanitary article which overcomes the problems of the prior art.

More specifically the object of the invention is to provide absorbent sanitary articles which employ a reduced quantity of elastic films and maintain good capacity of retention of body exudates.

According to the invention, this object is achieved by an absorbent sanitary article having the features of claim 1.

According to another aspect, the invention relates to a method for manufacturing absorbent sanitary articles having the features of claim 8.

The claims form an integral part of the technical disclosure provided here in relation to the invention.

BRIEF DESCRIPTION OF THE DRAWINGS

The present invention will now be described with reference to the attached drawings, provided purely by way of non-limiting example, wherein.

It should be appreciated that the attached drawings are schematic and not to scale with respect to real products. Various figures may not be represented in the same scale. Also, in various figures some elements may not be shown to better show other elements.

DETAILED DESCRIPTION

Figure 1:
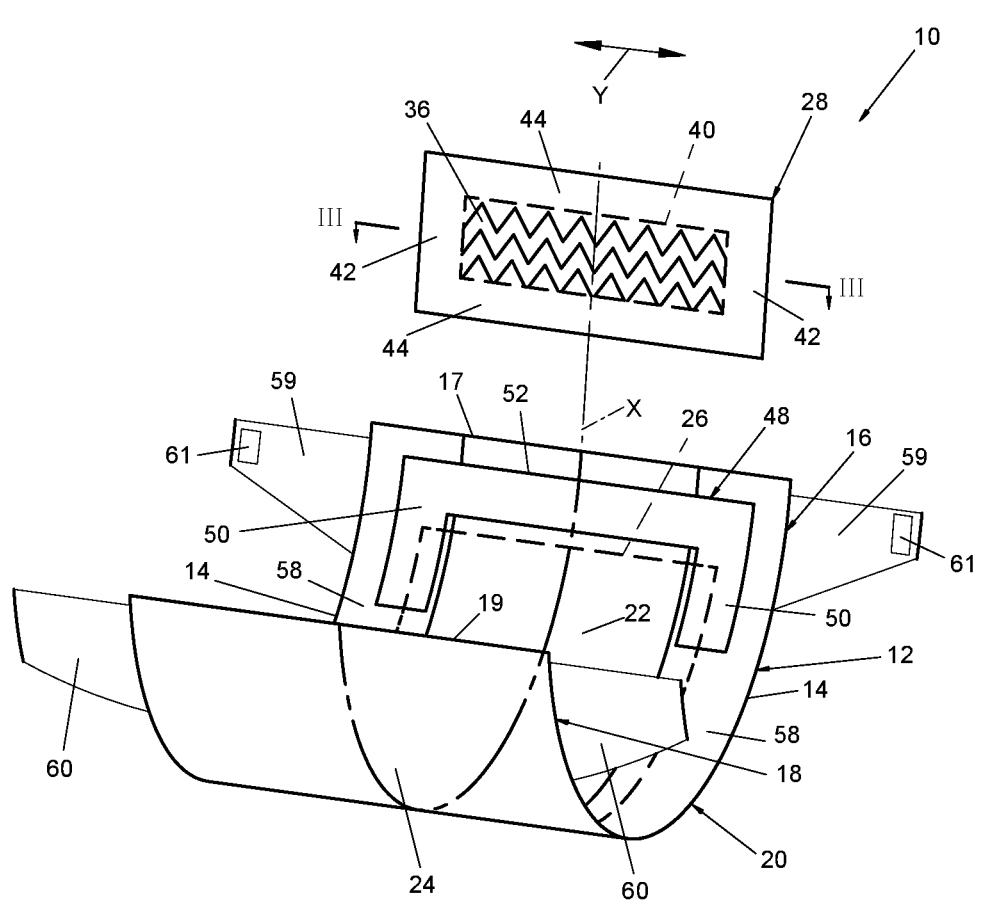
FIG. 1 is a partially exploded perspective view of an absorbent sanitary article according to an embodiment of the invention.
Figure 2:
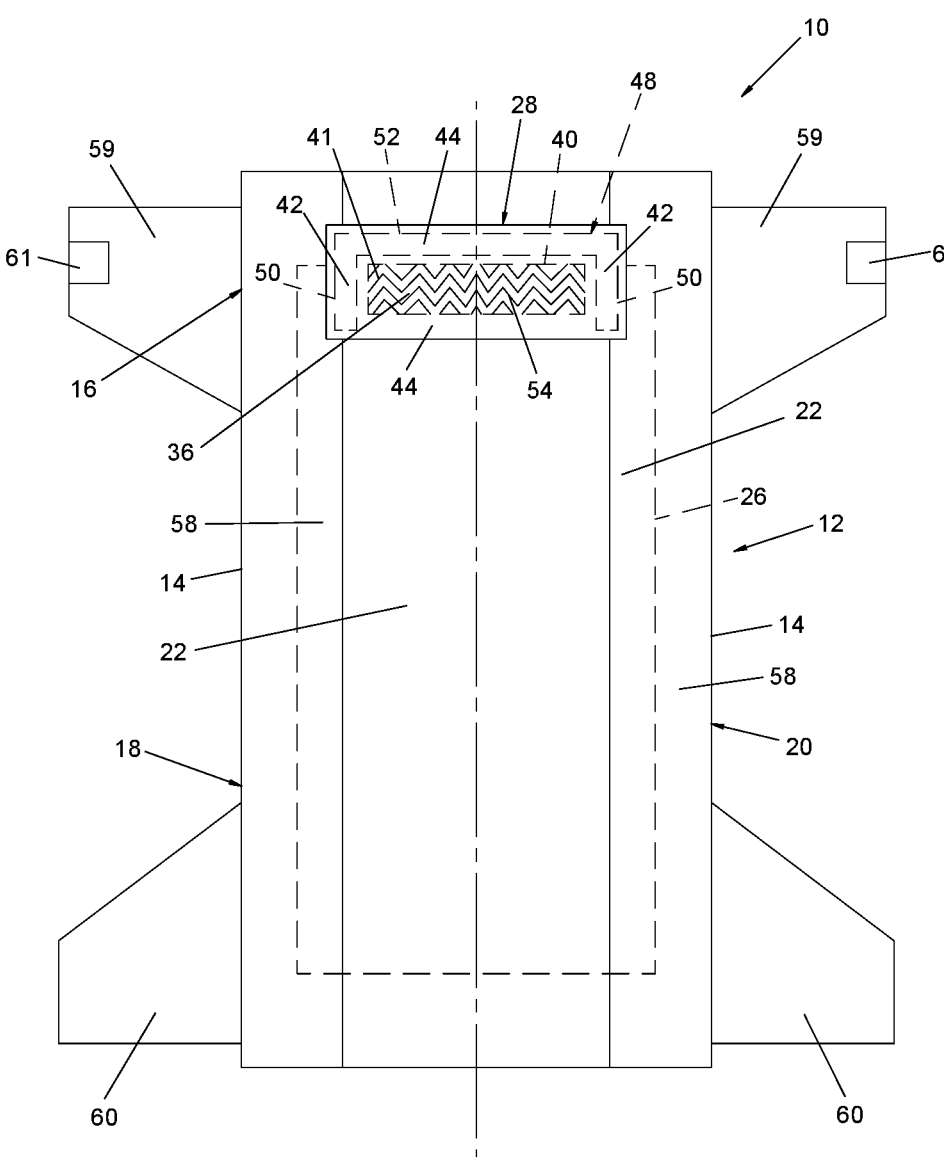
FIG. 2 is a schematic plan view showing the absorbent sanitary article of FIG. 1 in an extended position.

With reference to FIGS. 1 and 2, numeral 10 indicates an absorbent sanitary article according to the present invention. FIG. 1 shows the absorbent sanitary article 10 in the configuration in which it is worn, and FIG. 2 shows the absorbent sanitary article 10 in a flat configuration.

The absorbent sanitary article 10 comprises a chassis 12 elongated along a longitudinal axis X. The chassis 12 has two side edges 14, and rear and front waist sections 16, 18. The rear and front waist sections 16, 18 have respective transverse edges 17, 19. The rear and front waist sections 16, 18 may be not elastic. A crotch section 20 extends between the rear and front waist sections 16, 18. In use, the rear and front waist sections 16, 18 are closed around the user's waist and the crotch section 20 is arranged between the user's legs.

The chassis 12 may have a rectangular shape, with two straight side edges 14 parallel to the longitudinal axis X. In a possible embodiment, the side edges 14 may be shaped so as to conform to the legs of the user in the configuration in which the absorbent sanitary article 10 is worn, such that in a flat configuration the absorbent sanitary article 10 has substantially an hourglass shape.

The chassis 12 comprises a topsheet 22 made of a permeable material having an outer surface which, in use, is in contact with the user's skin, an impermeable backsheet 24, and an absorbent core 26 set between the topsheet 22 and the backsheet 24.

The absorbent sanitary article 10 comprises at least one gasketing element 28 elastically stretchable in a transverse direction Y orthogonal to the longitudinal axis X. In FIG. 1 the gasketing element 28 is shown in an exploded position with respect to the chassis 12. The gasketing element 28 is applied on the outer surface of the topsheet 22 in at least one of the rear and front waist sections 16, 18. In a possible embodiment, the absorbent sanitary article 10 may comprise rear and front gasketing elements 28 attached respectively to the rear and front sections 16, 18 of the chassis 12.

Figure 3:
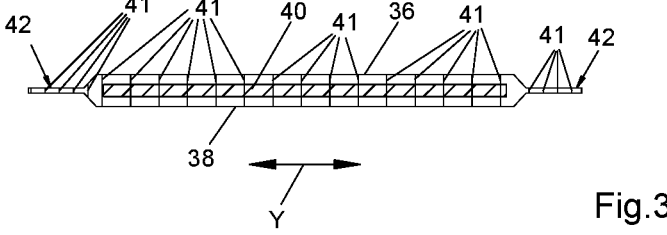
FIG. 3 is a schematic cross-section of a gasketing element taken along the line III-III of FIG. 3.

With reference to FIGS. 1 and 3, the gasketing element 28 comprises two non-elastic outer layers 36, 38 and at least one transversally stretchable elastic film 40 sandwiched between the two non-elastic outer layers 36, 38.

The two non-elastic outer layers 36, 38 may be joined to the transversally stretchable elastic film 40, by ultrasonic welding, thermocompression welding or by glue. In a possible embodiment, the two non-elastic outer layers 36, 38 may be joined to the transversally stretchable elastic films 40, by a pattern of ultrasonic spot welds 41. The spot welds 41 may form through holes in the transversally stretchable elastic film 40 and the two non-elastic outer layers 36, 38 may be fixed to each other through the through holes.

The gasketing element 28 may comprise a non-elastic outer layer 36 of non-woven material and a non-elastic outer layer 38 of impermeable plastic material. The non-elastic outer layer 38 of impermeable plastic material may forms the surface of the gasketing element 28 facing the outer surface of the topsheet 22. The non-elastic outer layer 36 of non-woven material may form the surface of the gasketing element 28 which in use is in contact with the user's skin.

With reference to FIGS. 1 to 3, the transversally stretchable elastic film 40 is shorter than the two non-elastic outer layers 36, 38 both in the direction of the longitudinal axis X and in a transverse direction Y orthogonal to the longitudinal axis X. Therefore, the gasketing element 28 has two non-elastic longitudinal portions 42 and two non-elastic transverse portions 44 forming a non-elastic frame surrounding the transversally stretchable elastic film 40.

With reference to FIG. 3, in the non-elastic longitudinal transverse portions 42, 44 the transversally stretchable elastic film 40 is not present and the two non-elastic outer layers 36, 38 are fixed directly to each other, e.g. by the same pattern of spot welds 41 that joins the two non-elastic outer layers 36, 38 to the transversally stretchable elastic film 40.

With reference to FIG. 1, the or each gasketing element 28 is attached to the rear and/or front waist section 16, 18 the chassis 12 along a C-shaped attachment profile 48 including two opposite longitudinal portions 50 and a transverse outer portion 52.

The C-shaped attachment profile 48 may be formed by glue or by welding or a combination thereof. In a possible embodiment, the transverse outer portion 52 of the C-shaped attachment profile 48 may be formed by glue and the two opposite longitudinal portions 50 may be formed by welding, e.g. ultrasonic welding. In a possible embodiment, the two opposite longitudinal portions 52 of the C-shaped attachment profile 48 may include both glue and welding.

In a possible embodiment the two non-elastic longitudinal portions 42 of the gasketing element 28 are overlapped to the two opposite longitudinal portions 52 of the C-shaped attachment profile 48 and the outer non-elastic transverse portion 44 of the gasketing element 28 is overlapped to the transverse outer portion 52 of the C-shaped attachment profile 48 so that the portion of the gasketing element 28 containing the elastic element 40 is not attached to the chassis 12.

With reference to FIG. 2, a central inner region 54 of the elastic gasketing portion 30 is detached from the outer surface of the topsheet 22. The central inner region 54 of the gasketing element 28 is bordered on three sides by the C-shaped attachment profile 48 and is detached from the outer surface of the topsheet 22 to form a pocket open toward the crotch section 20.

With reference to FIG. 2, in a possible embodiment the gasketing element 28 has a width W1 in the transverse direction Y which is less than the width W2 in the transverse direction Y of the corresponding rear or front section 16, 18 of the chassis 12.

With reference to FIGS. 1 and 2 the absorbent sanitary article 10 may comprise two elastic leg cuffs 58. The leg cuffs 58 are sometimes also referred to as leg bands, side flaps, barrier cuffs, elastic cuffs or gasketing cuffs. The elastic leg cuffs 58 may be formed as disclosed in U.S. Pat. Nos. 3,860,003, 4,909,803, 4,695,278, 4,795,454, 4,704, 115, and US2009/0312730 A1.

The elastic leg cuffs 58 may comprise a plurality of elastic wires which are fixed, e.g. by glue, at discrete points to two opposite non-woven layers. The non-woven layers of the elastic leg cuffs 58 have respective outwardly facing longitudinal edges which are fixed, e.g. by glue, to the inner surface of the topsheet 22. The elastic leg cuffs 58 have respective inwardly facing longitudinal edges detached from the inner surface of the topsheet 22, which in use are in contact with the legs of the user to form barriers which help reduce the leakage of liquid, solid or semi-solid body exudates in the leg regions.

The elastic leg cuffs 58 may be configured in various ways. In a possible embodiment the elastic leg cuffs 58 may be formed separately from the topsheet 22 by sandwiching longitudinally stretched elastic wires between two non-woven layers. The longitudinally tensioned elastic wires are fixed in discrete points to the two non-woven layers by glue or by welds forming mechanical anchoring points, e.g. as disclosed in EP3092997 and U.S. Pat. No. 6,291,039. Between the longitudinally spaced fixing points the elastic wires are free to contract, so that the two non-woven layers assume a pleated shape when the elastic tension of the elastic wires is released. The elastic leg cuffs 58 may also be formed by folding portions of the topsheet 22 laterally inward, i.e., toward the longitudinal axis X, to form both the leg cuffs 58 and the side edges 14 of the chassis 12. In another example, the leg cuffs 58 may be formed by attaching an additional non-woven layer or layers to the chassis 12 at or adjacent to each of the respective side edges 14 of the chassis 12. The leg cuffs 58 may extend to the same longitudinal extent as the chassis 12 or alternatively the leg cuffs 34 may have a longitudinal extent that is less than that of the chassis 12.

With reference to FIGS. 1 and 2, the two non-elastic longitudinal portions 42 of the gasketing element 28 may be fixed to end portions of respective elastic leg cuffs 58.

The absorbent sanitary article 10 may comprise pairs of rear and front side panels 59, 60 projecting laterally beyond the side edges 14 of the rear and front sections 16, 18. The rear side panels 59 may carry respective fastening formations 61, formed for example by micro-hook elements. The front side panels 60 may have a surface of loop material (e.g. a non-woven material) for connection with the micro-hook fastening formations 61 of the rear side panels 59. The rear and/or front side panels 59, 60 may be elastically stretchable in the transverse direction Y.

When the absorbent sanitary article 10 is worn, the back and front side panels 59, 60 close the rear and front sections 16, 18 of the chassis 12 around the user's waist. The or each gasketing element 28 is in contact with the back and/or front waist regions of the user. The outer layer 36 of the gasketing element 28 is kept in contact with the user's skin. The outer layer 36 of the gasketing element 28 may be formed by a layer of non-woven material to provide a soft feeling against the user's skin.

The central inner region 54 of the gasketing element 28 forms an inwardly open pocket between the outer surface of the topsheet 22 and the gasketing element 28. Such pocket helps containing liquid, solid or semi-solid body exudates in the back and/or front waist region. The outer layer 38 of the gasketing element 28 facing the topsheet 22 may be of impermeable plastic material to form an impermeable barrier which helps containing body exudates in said pocket.

The elastic leg cuffs 58 may draw inwardly the inner edge of the gasketing element 28 so as to distance the inner surface of the gasketing element 28 from the topsheet 22, which has the effect of opening the pocket.

Figure 4:
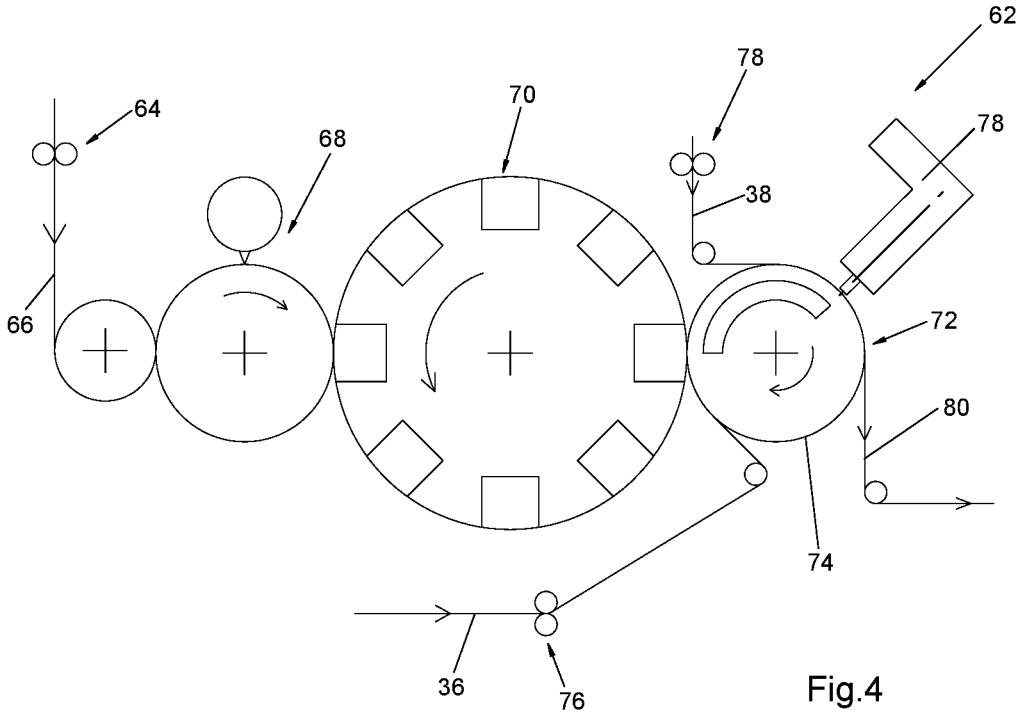
FIG. 4 is a schematic side view of an embodiment of an apparatus for producing a continuous elastic laminate.

The gasketing elements 28 may be manufactured by an apparatus 62 schematically shown in FIG. 4.

The apparatus 62 comprises a first feeding device 64 configured to feed a continuous elastic film 66 in a direction parallel to its longitudinal axis.

The apparatus 62 comprises a cut-and-slip unit 68 which transversely cuts from the continuous elastic film 66 individual elastic elements 40. The cut- and slip unit 68 spaces longitudinally from each other the individual elastic elements 40. The apparatus 62 comprises a transfer wheel 70 which picks-up the longitudinally spaced elastic elements 40 from the cut- and slip unit 68. The transfer wheel 70 may be provided on its outer surface with suction holes to hold the longitudinally spaced elastic elements 40.

The apparatus 62 comprises an anvil wheel 72 having an outer cylindrical surface 74 provided with suction holes pneumatically connected to a source of sub-atmospheric pressure.

The apparatus 62 comprises second and third feeding devices 76, 78 configured to feed to the outer cylindrical surface 74 of the anvil wheel 72 first and second continuous non-elastic layers 36, 38.

The transfer wheel 70 applies the longitudinally spaced elastic elements 40 on first continuous non-elastic layer 36 on the outer cylindrical surface 74 of the anvil wheel 72, where they are retained by suction.

The second continuous non-elastic layer 38 is overlapped to the first continuous non-elastic layer 36 over the longitudinally spaced elastic elements 40, so that the elastic elements 40 spaced apart from each other are sandwiched between the first and second continuous non-elastic layers 36, 38. In a transverse direction the first and second continuous non-elastic layers 36, 38 are wider than the transversely stretched elastic elements 40.

The apparatus 62 comprises a fastening device 78 cooperating with the outer cylindrical surface 74 of the anvil wheel 72. The fastening device 78 may be an ultrasonic welding device, a pressure device for fastening by adhesive, or a thermal or thermomechanical welding device. The fastening device 78 joins the individual elastic elements 40 to the continuous non-elastic layers 36, 38 to form a continuous elastic laminate 80 which is then detached from the anvil wheel 72.

Figure 5:
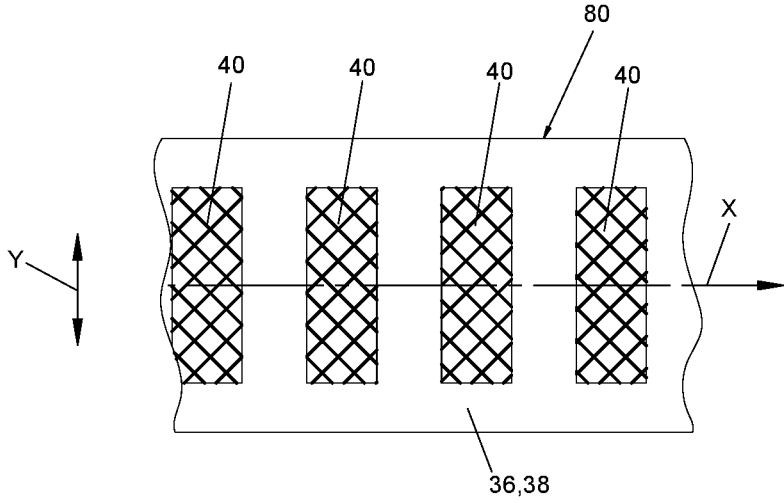
FIG. 5 is a partial plan view of a continuous elastic laminate.

With reference to FIG. 5, the continuous elastic laminate 80 comprises two continuous non-elastic outer layers 36, 38 and a plurality of elastic elements 40 elastically stretchable in a transverse direction Y and sandwiched between the two non-elastic outer layers 36, 38. The elastic elements 40 in the transverse direction Y are shorter than the non-elastic outer layers 36, 38 and are spaced apart from each other in the longitudinal direction X.

Figure 6:
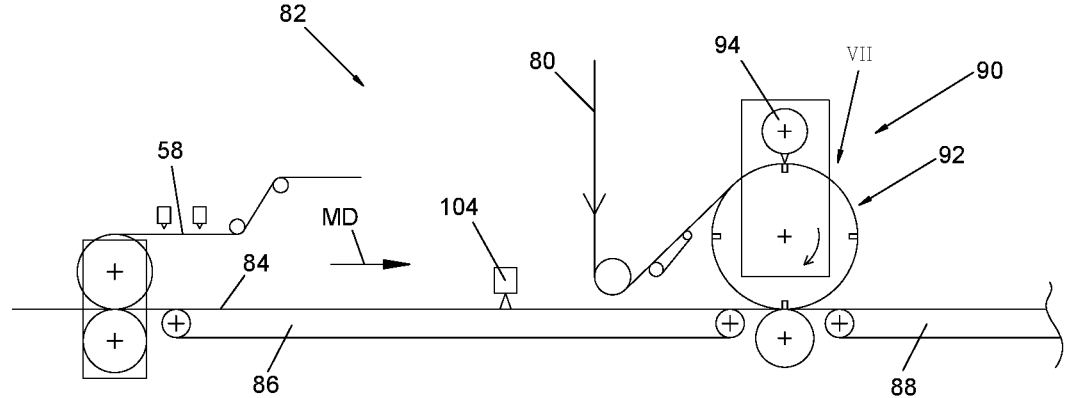
FIG. 6 is a schematic side view of an embodiment of a machine for manufacturing absorbent sanitary articles according to the invention.

FIG. 6 schematically shows a machine 82 for manufacturing absorbent sanitary articles.

The machine 82 is configured for forming an array of chassis 12. In the machine 82 the array of chassis 12 may be formed in the form of a continuous composite tape 84 which advances in a machine direction MD, on conveyors 86, 88. The continuous composite tape 84 may include a pair of continuous elastic leg cuffs 58 and pairs of front and rear side panels 59, 60.

With reference to FIG. 6, the continuous elastic laminate 80 exiting the apparatus 62 of FIG. 4 may be supplied in-line to the machine 82 for manufacturing absorbent sanitary articles.

Alternatively, at the exit of the apparatus 62 of FIG. 4 the continuous elastic laminate 80 may be collected in reels which are stored and transported to machines 82 for manufacturing absorbent sanitary articles. In this case, the continuous elastic laminate 80 which supplies the machine 82 is unwound from a reel in an unwinding device (not shown).

With reference to FIG. 6, in the machine 82 the continuous elastic laminate 80, supplied either in-line or unwound from a reel, is transversely cut in a cut-and-slip unit 90 to form individual gasketing elements 28. A glue dispenser (not shown) may be provided poststream of the cut-and-slip unit 90 for applying a glue pattern on the continuous elastic laminate 80.

The cut-and-slip unit 90 comprises an anvil wheel 92 cooperating with a rotating knife 94.

Figure 7:
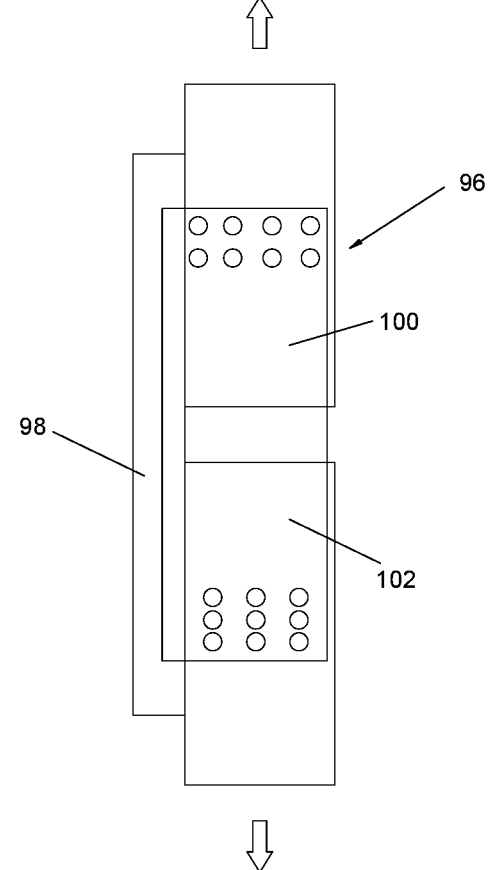
FIG. 7 is a plan view of the detail indicated by the arrow VII in FIG. 6.

With reference to FIG. 7, the anvil wheel 92 comprises a plurality of gripping elements 96 adjacent to respective anvil elements 98. The anvil elements 98 cooperate with the rotating knife 94 to transversely cut the continuous elastic laminate 80. The individual gasketing elements 28 formed by cutting the continuous elastic laminate 80 are retained by respective gripping elements 96. The gripping elements 96 move with a speed greater than the speed of the continuous elastic laminate 80, so that the individual gasketing elements 28 are spaced apart from each other in the longitudinal direction. Each of the gripping elements 96 includes two gripping pads 100, 102 configured for retaining, e.g. by suction, respective portions of the respective individual gasketing elements 28. The two gripping pads 100 of each gripping element 96 are movable in the transverse direction Y apart from each other, so as to transversally stretch the respective gasketing elements 28. The transverse movement of the two gripping pads 100, 102 may be controlled by a cam.

With reference to FIG. 5, the anvil wheel 92 applies the transversely stretched gasketing elements 28 on the continuous composite tape 84 moving in the machine direction MD in positions longitudinally spaced from each other.

A glue dispenser 104 may be provided for intermittently dispensing glue layers on the continuous composite tape 84 upstream of the anvil wheel 92.

The individual gasketing elements 28 are attached to the array of chassis 12 such that the gasketing elements 28 extends between the two side edges 14 of the respective chassis 12. Each gasketing element 28 is attached, e.g. by glue, to the outer surface of the topsheet 22 of a respective chassis along a C-shaped attachment profile as disclosed with reference to FIGS. 1 and 2, so that a central inner region 54 of the gasketing element 28 is detached from the outer surface of the topsheet 22 to form a pocket open toward the crotch section 20.

Of course, without prejudice to the principle of the invention, the details of construction and the embodiments can be varied, even significantly, with respect to those illustrated here without departing from the scope of the invention as defined by the following claims.

The invention claimed is:

1. An absorbent sanitary article comprising:

a chassis having a longitudinal axis, two side edges, rear and front waist sections, and a crotch section intermediate between the rear and front waist sections, the chassis including a topsheet having an outer surface which in use is adapted to be in contact with a user's skin, a backsheet, and an absorbent core set between the topsheet and the backsheet, and at least one gasketing element applied on the outer surface of the topsheet in at least one of said rear and front waist sections, wherein the at least one gasketing element includes two non-elastic outer layers and a transversally stretchable elastic film sandwiched between said two non-elastic outer layers, wherein the two outer layers are separate and distinct layers fixed to each other to sandwich the transversally stretchable elastic film therebetween, wherein the transversally stretchable elastic film is shorter than the two non-elastic outer layers both in the direction of said longitudinal axis and in a transverse direction orthogonal to the longitudinal axis, so that the at least one gasketing element has two non-elastic longitudinal portions and two non-elastic transverse portions forming a non-elastic frame surrounding the transversally stretchable elastic film, wherein the at least one gasketing element is attached to the chassis along a C-shaped attachment profile including two opposite longitudinal portions and a transverse outer portion, wherein a central inner region of the at least one gasketing element is detached from the outer surface of the topsheet to form a pocket open toward said crotch section, wherein the central region includes the transversally stretchable elastic film such that the transversally stretchable elastic film is detached from the outer surface of the topsheet and is surrounded on three sides by the C-shaped attachment profile, and wherein the at least one gasketing element has a width in the transverse direction which is less than the width in the transverse direction of the respective rear and front waist sections of the chassis.

2. The absorbent sanitary article of claim 1, wherein the two non-elastic longitudinal portions of the at least one gasketing element are overlapped to said two opposite longitudinal portions of the C-shaped attachment profile.

3. The absorbent sanitary article of claim 1, wherein an outer non-elastic transverse portion of the at least one gasketing element is overlapped to said transverse outer portion of said C-shaped attachment profile.

4. The absorbent sanitary article of claim 1, wherein the chassis comprises a pair of elastic leg cuffs extending parallel to said longitudinal axis and attached to an inner surface of the topsheet, and wherein said two non-elastic longitudinal portions of the at least one gasketing element are fixed to respective end portions of said elastic leg cuffs.

5. The absorbent sanitary article of claim 1, wherein said at least one gasketing element comprises an outer layer of impermeable plastic material facing the outer surface of the topsheet.

6. The absorbent sanitary article of claim 1, wherein said at least one gasketing element comprises at least one layer of non-woven material forming a surface of the at least one gasketing element which in use is adapted to be in contact with the user's skin.

7. A method for producing absorbent sanitary articles, comprising:

providing a continuous elastic laminate elongated in a longitudinal direction and comprising two continuous non-elastic outer layers and a plurality of elastic elements sandwiched between the two non-elastic outer layers, wherein said plurality of elastic elements are elastically stretchable in a transverse direction and are spaced apart from each other in the longitudinal direction, and wherein the plurality of elastic elements in the transverse direction are shorter than the non-elastic outer layers, providing an array of chassis each having a longitudinal axis, two side edges, rear and front waist sections, and a crotch section intermediate between the rear and front waist sections, each chassis including a topsheet having an outer surface which in use is adapted to be in contact with a user's skin, a backsheet, and an absorbent core set between the topsheet and the backsheet, transversely cutting said continuous elastic laminate to form individual gasketing elements each including two non-elastic outer layers and a transversally stretchable elastic film sandwiched between said two non-elastic outer layers, wherein the two outer layers are separate and distinct layers fixed to each other to sandwich the transversally stretchable elastic film therebetween, wherein the transversally stretchable elastic film is shorter than the two non-elastic outer layers both in the direction of said longitudinal axis and in a transverse direction orthogonal to the longitudinal axis, so that each individual gasketing element has two non-elastic longitudinal portions and two non-elastic transverse portions forming a non-elastic frame surrounding the transversally stretchable elastic film, applying said individual gasketing elements on the outer surface of the topsheet of a respective chassis in at least one of said rear and front waist sections, and attaching said individual gasketing elements to respective chassis along a C-shaped attachment profile including two opposite longitudinal portions and a transverse outer portion, wherein a central inner region of the individual gasketing element is detached from the outer surface of the topsheet to form a pocket open toward said crotch section, wherein the central region includes the transversally stretchable elastic film such that the transversally stretchable elastic film is detached from the outer surface of the topsheet and is surrounded on three sides by the C-shaped attachment profile, and wherein said individual gasketing elements are formed with a width in the transverse direction which is less than the width in the transverse direction of the respective rear or front waist section of the chassis.

8. The method of claim 7, wherein providing a continuous elastic laminate, comprises:

providing a continuous elastic film having a longitudinal direction, transversely cutting said continuous elastic film along transverse cutting lines orthogonal to said longitudinal direction, to provide a plurality of individual elastic elements, spacing from each other said individual elastic elements in said longitudinal direction, sandwiching said individual elastic elements stretched in the transverse direction between two continuous non-elastic outer layers, and joining said individual elastic elements to said two continuous non-elastic outer layers.

9. The method of claim 7, wherein the two non-elastic longitudinal portions of each individual gasketing element are overlapped to the two opposite longitudinal portions of the respective C-shaped attachment profile.

10. The method of claim 7, comprising transversely stretching said individual gasketing elements before attaching said individual gasketing elements to respective chassis.

11. The method of claim 7, comprising providing said chassis with respective pairs of elastic leg cuffs extending parallel to said longitudinal axis and attached to an inner surface of the topsheet, and fixing said two non-elastic longitudinal portions of each individual gasketing element to end portions of said elastic leg cuffs.

12. The method of claim 7, wherein one of said two continuous non-elastic outer layers is made of impermeable plastic material.

13. The method of claim 7, wherein one of said two continuous non-elastic outer layers is made of a non-woven material.

* * * * *